US012758273B2

(12) United States Patent
Sun et al.

(10) Patent No.: US 12,758,273 B2
(45) Date of Patent: Oct. 13, 2026

(54) EXPANDING AND SHAPING DEVICE FOR CERVICAL SPINAL CANAL AND MOUNTING DEVICE

(71) Applicants: PEKING UNIVERSITY THIRD HOSPITAL, Beijing (CN); SHANGHAI SANYOU MEDICAL CO., LTD., Shanghai (CN)

(72) Inventors: Yu Sun, Beijing (CN); Feifei Zhou, Beijing (CN); Michael Mingyan Liu, Shanghai (CN); Xing Liu, Shanghai (CN); Yuli Ma, Shanghai (CN)

(73) Assignees: PEKING UNIVERSITY THIRD HOSPITAL, Beijing (CN); SHANGHAI SANYOU MEDICAL CO., LTD., Shanghai (CN)

( * ) Notice: Subject to any disclaimer, the term of this patent is extended or adjusted under 35 U.S.C. 154(b) by 0 days.

(21) Appl. No.: 18/640,061

(22) Filed: Apr. 19, 2024

(65) Prior Publication Data

US 2025/0082371 A1 Mar. 13, 2025

(30) Foreign Application Priority Data

Sep. 7, 2023 (CN) ......................... 202311157186.7

(51) Int. Cl.

*A61B 17/70* (2006.01)
*A61B 17/80* (2006.01)
*A61B 50/20* (2016.01)

(52) U.S. Cl.

CPC ........ *A61B 17/7071* (2013.01); *A61B 17/808* (2013.01); *A61B 50/20* (2016.02)

(58) Field of Classification Search

CPC .................................................. A61B 17/7071
See application file for complete search history.

(56) References Cited

U.S. PATENT DOCUMENTS

| | | | | |
|---|---|---|---|---|
| 11,826,082 | B1 * | 11/2023 | Perryman | A61L 31/022 |
| 2003/0050700 | A1 * | 3/2003 | Kihara | A61B 17/7071 623/17.11 |
| 2003/0125740 | A1 * | 7/2003 | Khanna | A61B 17/7071 606/280 |

(Continued)

FOREIGN PATENT DOCUMENTS

| | | |
|---|---|---|
| CN | 211355832 U | 8/2020 |
| CN | 112807070 A | 5/2021 |

(Continued)

OTHER PUBLICATIONS

Office Action mailed Apr. 2, 2024 in connection with Chinese Patent Application No. 202311157186.7, 20 pgs. (including translation).

(Continued)

*Primary Examiner* — David W Bates
(74) *Attorney, Agent, or Firm* — Chiesa Shahinian & Giantomasi PC

(57) ABSTRACT

An expanding and shaping device for cervical spinal canal and a mounting device are provided, including the first fixing part, the second fixing part, and the fasteners. The passing-through direction of the fasteners is consistent with the direction of the incision. The fasteners are nailed along a coronal surface. The fasteners pass through the second fixing hole to connect the lateral mass.

2 Claims, 9 Drawing Sheets

(56) References Cited

U.S. PATENT DOCUMENTS

2003/0212400 A1* 11/2003 Bloemer ............ A61B 17/7071 606/279
2004/0030388 A1* 2/2004 Null ................... A61B 17/7071 606/279
2005/0107877 A1* 5/2005 Blain ................. A61B 17/7071 623/17.11
2005/0131412 A1* 6/2005 Olevsky ............... A61B 17/808 606/295
2005/0149021 A1* 7/2005 Tozzi ................. A61B 17/7058 606/247
2005/0228326 A1* 10/2005 Kalfas ................ A61B 17/7007 602/19
2005/0273100 A1* 12/2005 Taylor ................ A61B 17/7044 623/17.11
2006/0247633 A1* 11/2006 Winslow ............ A61B 17/8042 606/907
2006/0293662 A1* 12/2006 Boyer, II ........... A61B 17/1671 606/249
2007/0123863 A1* 5/2007 Winslow .............. A61B 17/025 606/255
2008/0033557 A1* 2/2008 Pasquet .............. A61B 17/7071 623/17.16
2008/0215096 A1* 9/2008 Nash .................. A61B 17/8042 606/249
2010/0057127 A1* 3/2010 McGuire ............ A61B 17/8023 606/70
2010/0069960 A1* 3/2010 Chaput .............. A61B 17/7071 606/248
2012/0165942 A1* 6/2012 Khanna .............. A61B 17/7071 623/17.16
2012/0271359 A1* 10/2012 Stevenson ............. A61F 2/2846 606/280
2012/0316647 A1* 12/2012 Farin ..................... A61F 2/4405 623/17.13
2013/0060283 A1* 3/2013 Suh .................... A61B 17/7007 606/246
2014/0114361 A1* 4/2014 Robinson ........... A61B 17/3468 606/281
2015/0265317 A1* 9/2015 Ricica ................ A61B 17/7071 606/279
2016/0135854 A1* 5/2016 Khanna .............. A61B 17/7071 606/280
2017/0311994 A1* 11/2017 Jung .................. A61B 17/8023
2017/0319244 A1* 11/2017 Prats Galino ...... A61B 17/7071
2018/0185078 A1* 7/2018 Na ..................... A61B 17/7071
2019/0083146 A1* 3/2019 Perryman .......... A61B 17/8858
2019/0175229 A1* 6/2019 Donner .............. A61B 17/7043
2020/0138487 A1* 5/2020 Suh .................... A61B 17/7044
2020/0179129 A1* 6/2020 Lauf ................... A61F 2/30749
2022/0061901 A1* 3/2022 Linder ............... A61B 17/8004
2023/0034622 A1* 2/2023 Park ................... A61B 17/7071
2023/0240727 A1* 8/2023 Giordano ........... A61B 17/7037 606/248
2024/0358416 A1* 10/2024 Jenkins, III ........ A61B 17/7044

FOREIGN PATENT DOCUMENTS

CN 215651469 U 1/2022
CN 115444527 A 12/2022
KR 100942170 B1 2/2010
KR 20130031584 A 3/2013

OTHER PUBLICATIONS

Notification of Grant of Invention Patent mailed Jun. 18, 2024 in connection with Chinese Patent Application No. 202311157186.7, 6 pgs. (including translation).

* cited by examiner

EXPANDING AND SHAPING DEVICE FOR CERVICAL SPINAL CANAL AND MOUNTING DEVICE

CROSS-REFERENCES TO RELATED APPLICATIONS

This application claims the benefit of priority under 35 U.S.C. 119 to Chinese Patent Application No. 2023111571867, filed Sep. 7, 2023; the disclosure of which is incorporated herein by reference in its entirety.

TECHNICAL FIELD

The present disclosure relates to the technical field of medical devices, and in particular relates to an expanding and shaping device for the cervical spinal canal and mounting device.

BACKGROUND ART

Currently, only one side of the vertebral plate is incised in some posterior cervical spinal canal shaping surgeries and is retracted in an oblique rear direction to expand an area of the spinal canal, so as to loose the compressed nerves and relieve pain of patients. This kind of surgery to incise one side of the vertebral plate is a single-door surgery. This kind of single-door surgery usually enables the vertebral plates to be deflected towards a side direction, that is, a spinous process on the vertebral plate will be deflected towards the side direction and away from the original positions. Since the original position of the spinous process on the vertebral plate is in a middle region of a vertebral body on the cross section of the human body, the lateral mass will be forced unevenly by adopting the single-door surgery, and therefore the stress stability of the vertebral body is problematic after the single-door surgery.

In the prior art, vertebral plate nails are nailed into the vertebral plate in vertical direction. However, the method of nailing the vertebral plate nails in the vertical direction has a higher requirement for an incision size, and the vertebral plate nail has a smaller holding force. Moreover, the vertebral plate is lifted in a oblique direction, which is inconvenient for the doctor to operate.

SUMMARY

An objective of the present disclosure is to provide an expanding and shaping device for cervical spinal canal and a mounting device to solve the technical problems existing in the prior art that the incision when nailing the vertebral plate nail into the vertebral plate vertically has a higher size requirement, the vertebral plate nail has a small holding force, and a lifting operation is inconvenient.

An expanding and shaping device for cervical spinal canal provided by the present disclosure is configured to expand, shape, and fix a vertebral plate and a lateral mass formed by incising the cervical spinal canal, wherein a vertical incision is formed between the vertebral plate and the lateral mass, and the expanding and shaping device for cervical spinal canal includes a first fixing part, a second fixing part, and fasteners;

- the first fixing part is hinged to the second fixing part, wherein the first fixing part can be attached to a side wall of the vertebral plate, and the second fixing part is attached to a side surface of the lateral mass towards the vertebral plate; and
- a plurality of fasteners are provided, and a first fixing hole is arranged on the first fixing part, wherein the fasteners pass through the first fixing hole to connect the vertebral plate, and a passing-through direction of the fasteners is consistent with a direction of the incision; and the second fixing hole is arranged in the second fixing part, wherein the fasteners pass through the second fixing hole to connect the lateral mass.

In the preferred embodiment of the present disclosure, the first fixing part includes a fixing member and an extension member, wherein

- the fixing member is fixedly connected to the extension member, wherein the fixing member is provided with an inclined concave surface; the fixing member is attached to a side wall of the vertebral plate by the inclined concave surface; and one side of the fixing member away from the inclined concave surface is arranged in a horizontal plane, wherein the first fixing hole passes through vertically along the horizontal plane, and the fasteners can pass through the inclined concave surface from the horizontal plane so that the fasteners are tightly connected to the vertebral plate; and
- the extension member is arranged parallel to the incision so that the extension member can extend along a surface of the incision.

In the preferred embodiment of the present disclosure, the second fixing part includes a hinge member and a positioning member, wherein

- the hinge member is connected to the positioning member, and the hinge member is provided with a rotating shaft, wherein the extension member is rotationally connected to the hinge member by the rotating shaft; and the positioning member is attached to a surface of the lateral mass, wherein the second fixing hole passes through the positioning member, and the fasteners are connected to the lateral mass by the second fixing hole to fix the positioning member on the lateral mass.

In the preferred embodiment of the present disclosure, the positioning member is provided with a step, and the positioning member is snapped with one side of the lateral mass provided with the incision by the step.

In the preferred embodiment of the present disclosure, one side of the positioning member away from the step is provided with a first inclined surface, and one end of the extension member away from the fixing member is provided with a second inclined surface, wherein the extension member contacts and is limited by the first inclined surface of the positioning member by the second inclined surface, so as to limit the extension member to be in planar contact with the incision of the vertebral plate by the positioning member.

In the preferred embodiment of the present disclosure, one side of the first fixing part towards the second fixing part is provided with an accommodation groove, wherein the second fixing part can be attached and fixed with the accommodation groove; and

- clamping holes configured for cooperating with an external holder are arranged on two opposite sides of the first fixing part.

The present disclosure provides a mounting device, which is applicable to cooperate with the expanding and shaping device for cervical spinal canal, including a holding mechanism, wherein

- the holding mechanism is connected to the clamping holes in a cooperation method so that the first fixing part is attached to the vertebral plate which completes the incision.

In the preferred embodiment of the present disclosure, the holding mechanism includes a holder and a fastening mechanism, wherein the holder is provided with clamping ends, wherein the clamping ends can clamp two sides of the first fixing part, and the clamping ends can be snapped with the two clamping holes, respectively; and the fastening mechanism can cooperate with the fasteners, and the fastening mechanism is configured to drive the fasteners to pass through the first fixing hole and then to be nailed into the vertebral plate.

In the preferred embodiment of the present disclosure, the holder includes an adjusting part, and a first clamping part and a second clamping part hinged with each other, wherein the first clamping part and the second clamping part can be rotated relative to a hinged point to adjust a clamping range of the clamping ends; and one end of the adjusting part is rotationally connected to one end of the first clamping part away from the clamping ends, and the other end of the adjusting part can be snapped with one end of the second clamping part away from the clamping ends, so as to adjust the first clamping part and the second clamping part to be in a rotated or fixed state.

In the preferred embodiment of the present disclosure, the holder further includes a first elastic plate and a second elastic plate, wherein an adjusting space from the hinged point to the adjusting part is formed by the first clamping part and the second clamping part, and the first elastic plate and the second elastic plate are located within the adjusting space; and the first elastic plate is in an arcuate structure, and one end of the first elastic plate is provided with a slot, wherein one end of the first elastic plate away from the slot is connected to the first clamping part; the second clastic plate is in an arcuate structure, and one end of the second elastic plate is provided with a protrusion, wherein one end of the second elastic plate away from the protrusion is connected to the second clamping part; the second elastic plate can be inserted into the first elastic plate in a cooperation method by the slot and the protrusion, and the first elastic plate and the second elastic plate have an elastic tendency to move the first clamping part and the second clamping part away from each other so that the clamping ends have a tendency to move relatively close to each other.

The expanding and shaping device for cervical spinal canal provided by the present disclosure is configured to expand, shape, and fix the vertebral plate and the lateral mass formed by incising the cervical spinal canal. The vertical incision is formed between the vertebral plate and the lateral mass. The expanding and shaping device for cervical spinal canal includes the first fixing part, the second fixing part, and the fasteners. The first fixing part is hinged to the second fixing part, wherein the first fixing part can be attached to the side wall of the vertebral plate, and the second fixing part is attached to a side surface of the lateral mass towards the vertebral plate. The plurality of fasteners is provided. The first fixing hole is arranged in the first fixing part. The fasteners pass through the first fixing hole to connect the vertebral plate, and a passing-through direction of the fastener is consistent with the incision. The fasteners are nailed along a coronal surface so that the nail path is longer, and the holding force is improved, which is beneficial for a lifting operation for the vertebral plate and reduces the size requirement for the incision, such that wounds of patients are decreased. The second fixing hole is arranged on the second fixing part and the fasteners pass through the second fixing hole to connect the lateral mass. The fasteners separately passing through the first fixing part and the second fixing part are closer to the incision, so as to lower the notch, which solves the technical problems existing in the prior art that the incision when nailing the vertebral plate nail into the vertebral plate vertically has the higher size requirement, the vertebral plate nail has the small holding force, and the lifting operation is inconvenient.

BRIEF DESCRIPTION OF DRAWINGS

In order to more clearly illustrate embodiments of the present disclosure or technical solutions in the prior art, the drawings to be used in the description of the embodiments or prior art will be briefly introduced below. It is obvious that the drawings described in the following are some of the embodiments of the present disclosure. A person of ordinary skill in the art can obtain other relevant drawings according to these drawings without inventive efforts.

Reference numbers: 10—vertebral plate; 20—lateral mass; 30—incision; 100—first fixing part; 101—fixing member; 111—inclined concave surface; 121—horizontal plane; 131—accommodation groove; 141—clamping hole; 102—extension member; 112—second inclined surface; 200—second fixing part; 201—hinge member; 211—rotating shaft; 202—positioning member; 212—step; 222—first inclined surface; 300—fastener; 400—holding mechanism; 401—holder; 411—clamping end; 421—adjusting part; 431—first clamping part; 441—second clamping part;

451—hinged point; 461—first elastic plate; 4611—slot; 471—second elastic plate; 4711—protrusion; 402—fastening mechanism.

DETAILED DESCRIPTION OF EMBODIMENTS

The technical embodiments of the present disclosure will be clearly and completely described below in connection with embodiments. It is obvious that the embodiments described are partial embodiments of the present disclosure and not all embodiments. Based on the embodiments in the present disclosure, all the other embodiments obtained by a person of ordinary skill in the art without inventive efforts shall belong to the scope of protection of the present disclosure.

Figure 1:
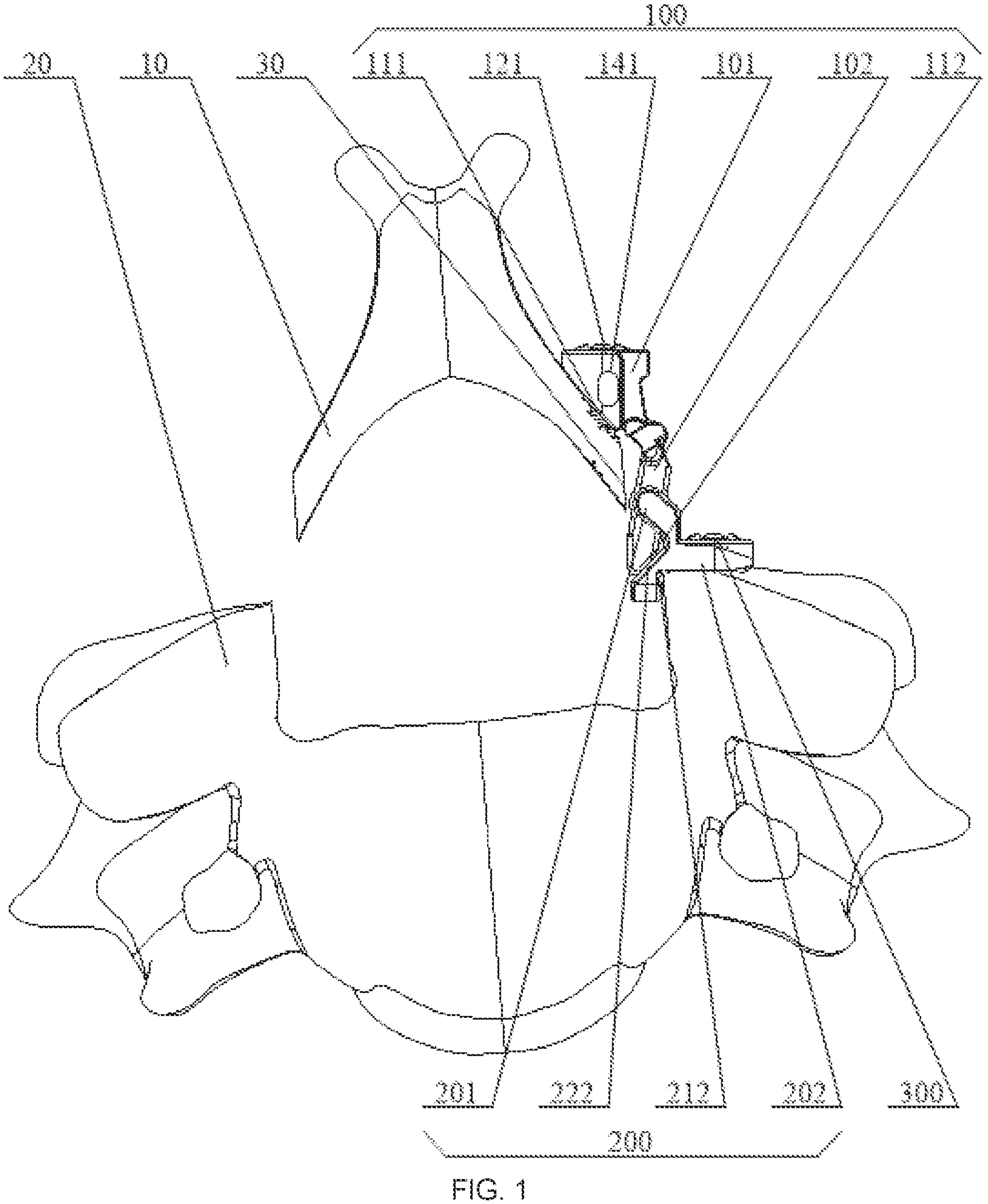
FIG. 1 is a structure schematic diagram of the expanding and shaping device for cervical spinal canal being mounted on the cervical spinal canal, provided by the embodiment of the present disclosure.
Figure 2:
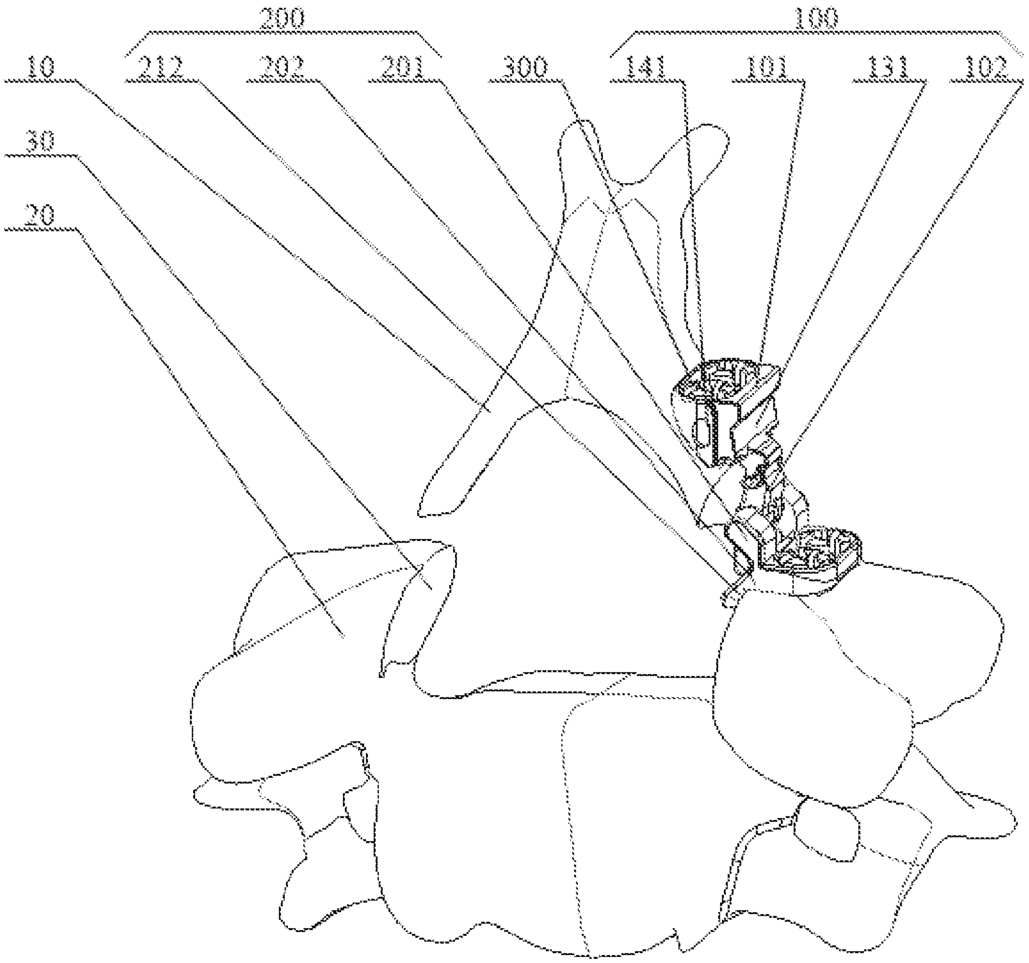
FIG. 2 is a structure schematic diagram of the expanding and shaping device for cervical spinal canal being mounted on the cervical spinal canal in the other view, provided by the embodiment of the present disclosure.
Figure 3:
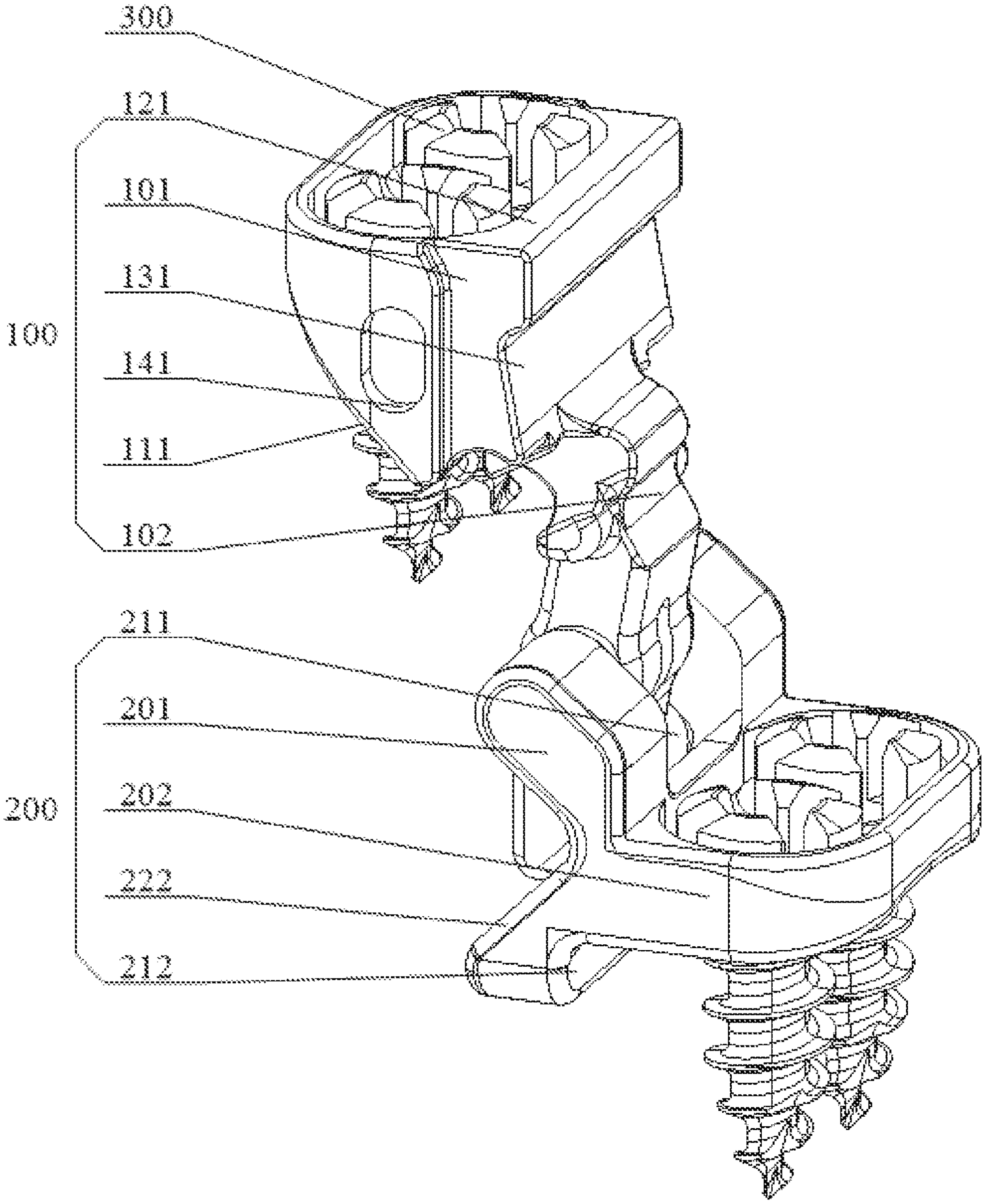
FIG. 3 is a structure schematic diagram of the expanding and shaping device for cervical spinal canal provided by the embodiment of the present disclosure.
Figure 4:
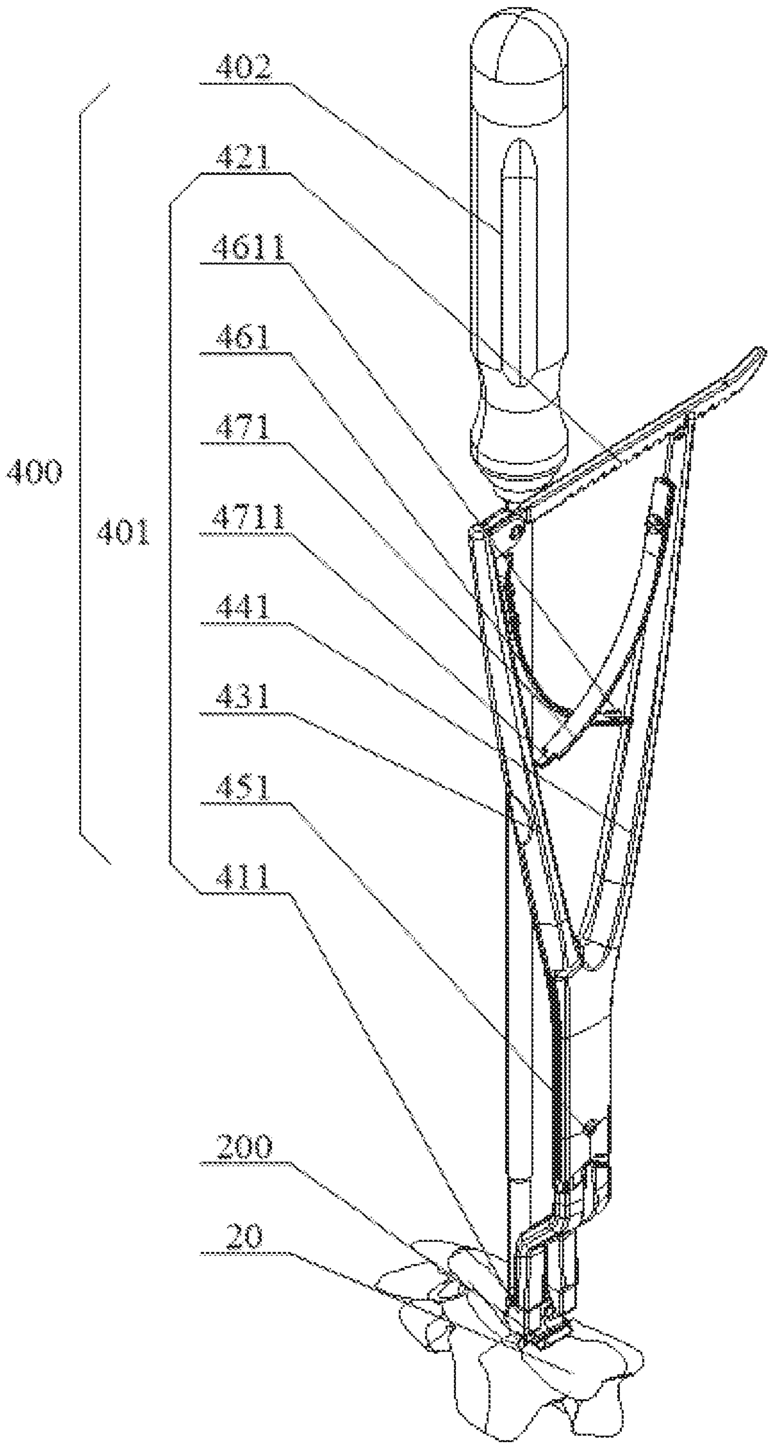
FIG. 4 is a structure schematic diagram of the expanding and shaping device for cervical spinal canal cooperating with a mounting device, provided by the embodiment of the present disclosure.
Figure 5:
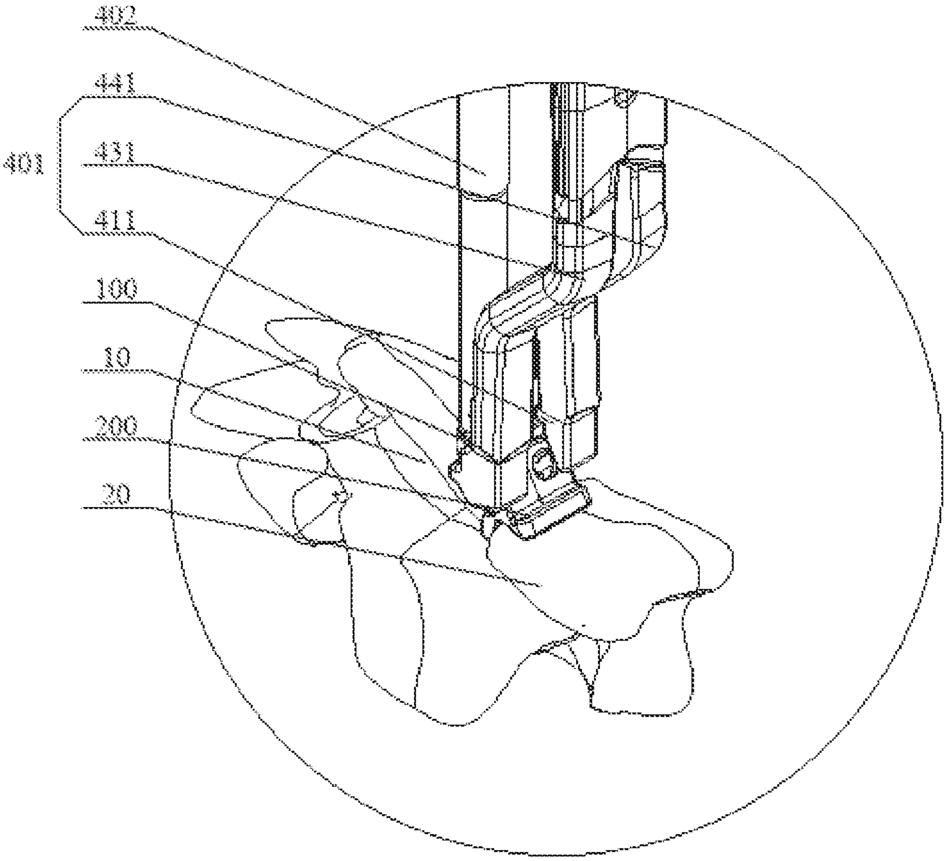
FIG. 5 is a schematic diagram of a locally enlarged structure of the expanding and shaping device for cervical spinal canal cooperating with a mounting device, provided by the embodiment in FIG. 4.
Figure 6:
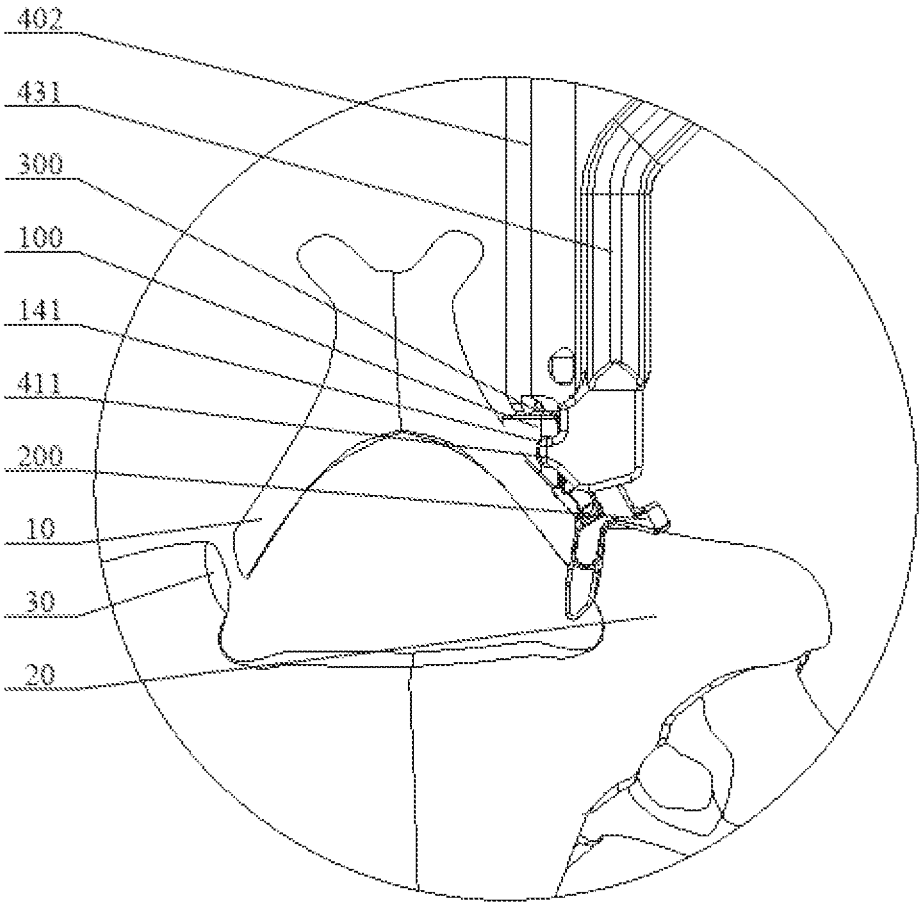
FIG. 6 is a schematic diagram of a locally enlarged structure of the expanding and shaping device for cervical spinal canal cooperating with a mounting device in the other view, provided by the embodiment in FIG. 4.
Figure 7:
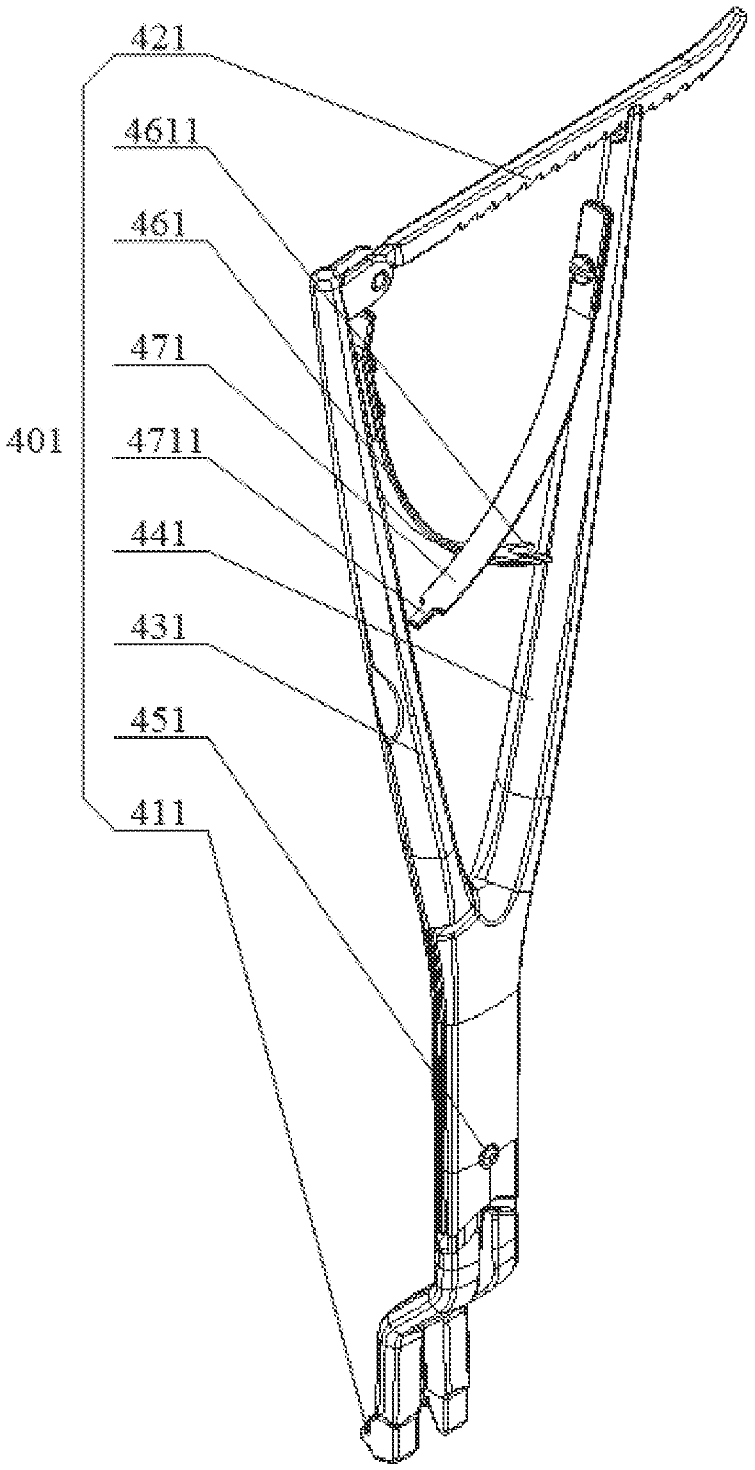
FIG. 7 is a structure schematic diagram of a holder when the expanding and shaping device for cervical spinal canal cooperates with the mounting device, provided by the embodiment of the present disclosure.
Figure 8:
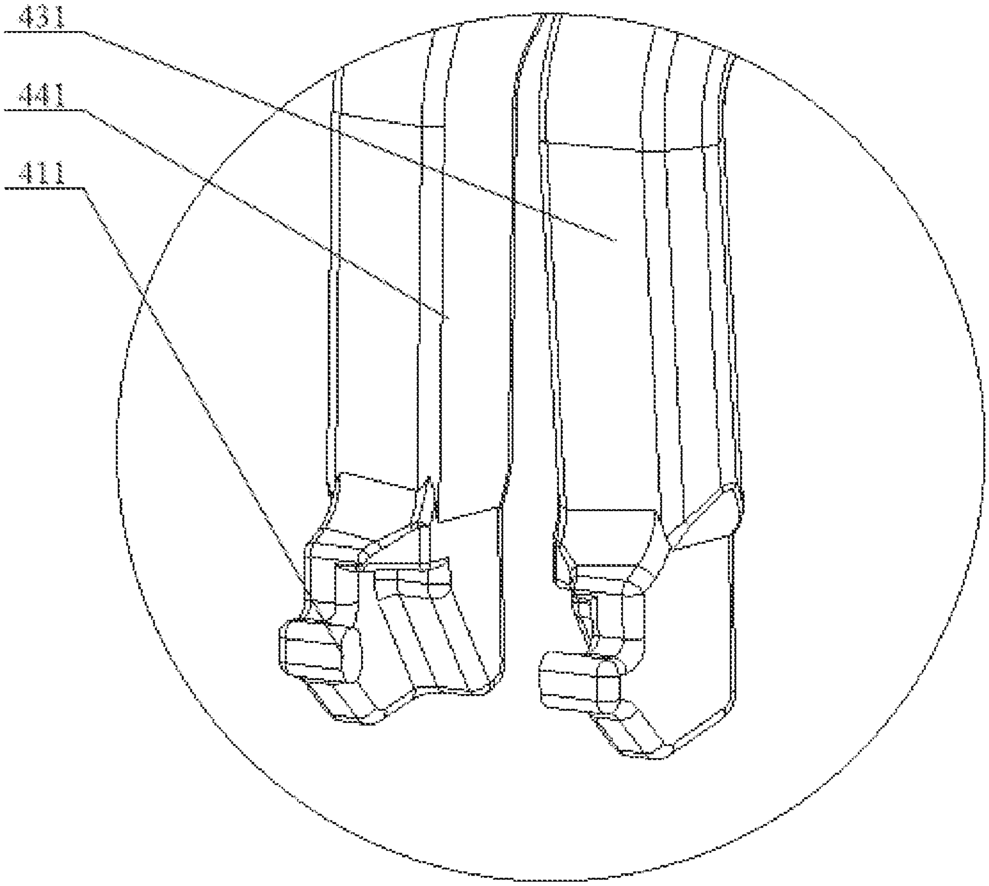
FIG. 8 is a schematic diagram of a locally enlarged structure of a holder when the expanding and shaping device for cervical spinal canal cooperates with the mounting device, provided by the embodiment in FIG. 7.
Figure 9:
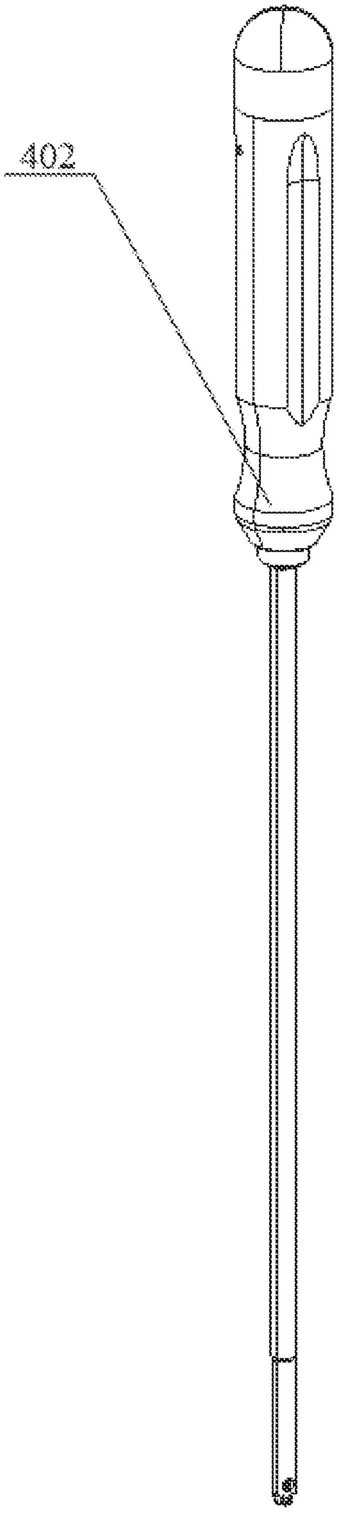
FIG. 9 is a structure schematic diagram of a fastening mechanism when the expanding and shaping device for cervical spinal canal cooperates with the mounting device, provided by the embodiment of the present disclosure.

As shown in FIG. 1-FIG. 9, an expanding and shaping device for cervical spinal canal provided by the embodiments is configured to expand, shape, and fix a vertebral plate 10 and a lateral mass 20 formed by incising the cervical spinal canal. The vertical incision 30 is formed between the vertebral plate 10 and the lateral mass 20. The expanding and shaping device for cervical spinal canal includes a first fixing part 100, a second fixing part 200, and fasteners 300. The first fixing part 100 is hinged to the second fixing part 200, wherein the first fixing part 100 can be attached to a side wall of the vertebral plate 10, and the second fixing part 200 is attached to a side surface of the lateral mass 20 towards the vertebral plate 10. A plurality of fasteners 300 are provided. A first fixing hole is arranged on the first fixing part 100. The fasteners 300 pass through the first fixing hole to connect the vertebral plate 10, and a passing-through direction of the fastener 300 is consistent with a direction of the incision 30. A second fixing hole is arranged in the second fixing part 200, and the fasteners 300 pass through the second fixing hole to connect the lateral mass 20.

It is noted that the expanding and shaping device for cervical spinal canal, provided in the embodiment, can be applied in a double-door spine lifting surgery for expanding and shaping the cervical spinal canal. The incision 30 on two sides of the vertebral plate 10 is formed, and thus the vertebral plate 10 and the lateral mass 20 are formed. The mounting device described below is utilized to drive a hinged position of the first fixing part 100 and the second fixing part 200 in folded states to be inserted in the incision 30. At this point, the first fixing part 100 can be attached to a side wall of the vertebral plate 10. The fasteners 300 are utilized to pass through the first fixing hole so that the fasteners 300 are nailed into the vertebral plate 10 along a direction parallel to the incision 30. The side wall of the vertebral plate 10 is arranged in an inclined method, and the incision 30 is in a vertical direction, that is, the nail paths can be increased by nailing the fasteners 300 along the vertical direction, which improves a holding force of the fasteners 300. At the same time, when the first fixing part 100 is utilized to lift the vertebral plate 10, it can be lifted straight along the vertical direction, which is beneficial for the lifting operation of the vertebral plate 10. At the same time, the nailing direction is the same as the direction of the incision 30, which is beneficial to reduce the size requirement of the incision 30, thereby reducing the wounds of the patients. When the vertebral plate 10 is lifted, the second fixing part 200 is rotated relative to the first fixing part 100, so that the second fixing part 200 is attached to a surface of the lateral mass 20. The fasteners 300 are then passed through the second fixing hole so that the fasteners 300 are nailed into the lateral mass 20. The lateral mass 20 is placed horizontally, that is, the second fixing part 200 is also arranged horizontally on the surface of the lateral mass 20. When the fasteners 300 at the second fixing part 200 are nailed, the fasteners 300 on the first fixing part 100 and the second fixing part 200 are arranged in parallel at this point, so that the two of them are closer to the incision 30, thereby reducing the notch. When a relative position at one side of the vertebral plate is fixed, it is sufficient to carry out the same operation on the other side of the vertebral plate 10.

Optionally, the fasteners 300 can be screws or bolts, etc. Preferably, the first fixing part 100 is provided with two first fixing holes, wherein the two first fixing holes are separately passed through by two fasteners 300 arranged side by side. Likewise, the second fixing part 200 is provided with two second fixing holes, wherein the two second fixing holes are separately passed through by two fasteners 300 arranged side by side. The two fasteners 300 on the first fixing part 100 are arranged side by side in a line, and the two fasteners 300 on the second fixing part 200 are arranged side by side in a line. The four fasteners 300 are arranged in parallel to each other, so that the four fasteners 300 can be close to the position of the incision 30, thereby reducing the notch.

The expanding and shaping device for cervical spinal canal provided by the embodiments is configured to expand, shape, and fix the vertebral plate 10 and the lateral mass 20 formed by incising the cervical spinal canal. The vertical incision 30 is formed between the vertebral plate 10 and the lateral mass 20. The expanding and shaping device for cervical spinal canal includes the first fixing part 100, the second fixing part 200, and the fasteners 300. The first fixing part 100 is hinged to the second fixing part 200, wherein the first fixing part 100 can be attached to the side wall of the vertebral plate 10, and the second fixing part 200 is attached to a side surface of the lateral mass 20 towards the vertebral plate 10. The plurality of fasteners 300 are provided. The first fixing hole is arranged in the first fixing part 100. The fasteners 300 pass through the first fixing hole to connect the vertebral plate 10, and the passing-through direction of the fastener 300 is consistent with the direction of incision 30. The fasteners 300 are nailed along the coronal surface, so that the nail path is longer and the holding force is improved, which is benefit for the lifting operation for the vertebral plate 10 and reduces the size requirement for the incision 30, such that wounds of patients are decreased. The second fixing hole is arranged in the second fixing part 200 and the fasteners 300 pass through the second fixing hole to connect the lateral mass 20. The fasteners 300 separately passing through the first fixing part 100 and the second fixing part 200 are closer to the incision 30, so as to lower the notch, which solves the technical problems existing in the prior art that the incision 30 when nailing the vertical plate 10 nail into the vertebral plate 10 vertically has the higher size requirement, the vertebral plate 10 nail has the small holding force, and the lifting operation is inconvenient.

In the preferred embodiment of the present disclosure, the first fixing part 100 includes a fixing member 101 and an extension member 102. The fixing member 101 is fixedly connected to the extension member 102. The fixing member 101 is provided with an inclined concave surface 111, and the fixing member 101 is attached to the side wall of the vertebral plate 10 by the inclined concave surface 111. One side of the fixing member 101 away from the inclined concave surface 111 is arranged as a horizontal plane 121. The first fixing hole passes through vertically along the horizontal plane 121. The fasteners 300 can pass through the inclined concave surface 111 from the horizontal plane 121 so that the fasteners 300 are tightly connected to the vertebral plate 10. The extension member 102 is arranged parallel to the incision 30 so that the extension member 102 can extend along the surface of the incision 30.

In this embodiment, the fixing member 101 can be adopted as a fixing block provided with the inclined concave surface 111. The sectional shape of the fixing member 101 is similar to a right-angled trapezoid, that is, a right angle is formed on one end of the fixing member 101 provided with horizontal plane 121; the fixing member 101 is provided with the inclined concave surface 111 to form an inclined surface; and one end of the fixing member 101 away from the extension member 102 is a short side, and one end of the fixing member 101 close to the extension member 102 is a long side. The fixing member 101 is attached and fixed to the side wall of the vertebral plate 10 by the inclined concave surface 111. At this point, the extension member 102 extends into the position of the incision 30, and the first fixing hole passes through along a direction from the horizontal plane 121 to the inclined concave surface 111. The extension direction of the first fixing hole is consistent with the direction of the incision 30, so the extension direction of the fastener 300 is also consistent with the direction of the incision 30 after the fasteners 300 are nailed into the vertebral plate along the first fixing hole, which facilitates the lifting operation along the incision 30. The extension member 102 is configured as a connecting structure between the fixing member 101 and the second fixing part 200. The extension member 102 can be extended along the surface of the incision 30, and the extension member 102 can be ensured to insert into the incision 30 and extend to the second fixing part 200.

Optionally, a plurality of connection methods of the fixing member 101 and the extension member 102 are provided, such as integrally molded, welded, or inserted, etc. Preferably, the fixing member 101 and the extension member 102 can be integrally molded by 3D printing.

In the preferred embodiment of the present disclosure, the second fixing part 200 includes a hinge member 201 and a positioning member 202. The hinge member 201 is connected to the positioning member 202, and the hinge member 201 is provided with a rotating shaft 211, wherein the extension member 102 is rotationally connected to the hinge member 201 by the rotating shaft 211. The positioning member 202 is attached to the surface of the lateral mass 20, and the second fixing hole passes through the positioning member 202. The fasteners 300 are connected to the lateral mass 20 by the second fixing hole to fix the positioning member 202 on the lateral mass 20.

In this embodiment, the hinge member 201 is provided with a groove, and a rotating shaft 211 is arranged in the groove. The extension member 102 is rotationally connected to the hinge member 201 by the rotating shaft 211, and a connection position of the extension member 102 and the rotating shaft 211 is at the middle part of the extension member 102, that is, one end of the extension member 102 away from the fixing member 101 is extended out of the groove to ensure that the extension member 102 can be extended into the position of the incision 30 when the first fixing part 100 and the second fixing part 200 are in a folded state. The positioning member 202 can be of a positioning block structure. After the positioning member 202 is attached to the surface of the lateral mass 20, the fasteners 300 pass through the second fixing hole. The positioning member 202 is tightly connected to the lateral mass 20 to complete the expanding, shaping, and fixing for the vertebral plate 10 and the lateral mass 20.

In this embodiment, the extension member 102 is movably connected to the hinge member 201 by the rotating shaft 211, so that the positioning member 202 can be rotated relative to the fixing member 101. The positioning member 202 can be flipped in free angles relative to the fixing member 101 to ensure that the first fixing part 100 and the second fixing part 200 can be in a folded state or an unfolded state, which can then be manufactured into a small and lightweight structure so that the size of the incision 30 can be effectively reduced and wounds of the patients are reduced. The following mounting device can realize the easy operation and shorten the surgical time, so as to improve the surgery safety, which is applied to the double-door spine lifting surgery so that the vertebral plate 10 is not shifted towards the side direction. In other words, it maintains the original physiological and mechanical structure of the human body. The vertebral body is stressed stably after the double-door spine lifting surgery, which is beneficial for better recovery of patients.

In the preferred embodiment of the present disclosure, the positioning member 202 is provided with a step 212, wherein the positioning member 202 is snapped with one side of the lateral mass 20 with the incision 30 by the step 212.

In this embodiment, the step 212 is located at one end of the positioning member 202 close to the hinge member 201. One end of the lateral mass 20 provided with the incision 30 can be snapped positionally by utilizing the step 212, which ensures that the extension member 102 can be completely extended into the position of the incision 30, so as to ensure the positioning requirements of the fixing member 101 and the positioning member 202.

In the preferred embodiment of the present disclosure, one side of the positioning member 202 away from the step 212 is provided with the first inclined surface 222, and one end of the extension member 102 away from the fixing member 101 is provided with the second inclined surface 112. The extension member 102 contacts and is limited by the first inclined surface 222 of the positioning member 202 by the second inclined surface 112 so as to limit the extension member 102 to be in planar contact with the incision 30 of the vertebral plate 10 by the positioning member 202.

In this embodiment, since the positioning member 202 needs to be free to flip relative to the fixing member 101, the positioning member 202 is connected to the extension member 102 by the first inclined surface 222 and the second inclined surface 112 to avoid interference between the extension member 102 and the positioning member 202. The first inclined surface 222 and the second inclined surface 112 can be inclined at 45°, respectively. That is to say, when the positioning member 202 completes the positioning with the lateral mass 20 by the step 212, the positioning member 202 and the extension member 102 abut against each other separately by the first inclined surface 222 and the second inclined surface 112. One side surface of the extension member 102 close to the fixing member 101 is in the vertical direction at this point, which ensures that the extension member 102 is attached to the surface of the incision 30.

In the preferred embodiment of the present disclosure, one side of the first fixing part 100 towards the second fixing part 200 is provided with an accommodation groove 131, wherein the second fixing part 200 can be attached and fixed with the accommodation groove 131. The clamping holes 141 configured for cooperating with the external holder 401 are arranged on two opposite sides of the first fixing part 100.

In this embodiment, during the initial mounting, the second fixing part 200 is in the folded state relative to the first fixing part 100 at this point. In order to ensure that the second fixing part 200 is attached and fixed to the first fixing part 100, one side of the first fixing part 100 towards the second fixing part 200 is provided with the accommodation groove 131, so that the volume of the first fixing part 100 and second fixing part 200 in the folded state meets entering along the wound. At the same time, the first fixing part 100 can be snapped and fixed with the holder 401 by the clamping hole 141, and the holder 401 can form a limit along a direction from the second fixing part 200 to the first fixing part 100. At the same time, the end part of the holder 401 can be snapped with the clamping holes 141, so that the first fixing part 100 and the second fixing part 200 can be conveniently mounted in place.

As shown in FIG. 4-FIG. 9, a mounting device cooperating with the expanding and shaping device for cervical spinal canal provided by the embodiment includes a holding mechanism 400, wherein the holding mechanism 400 is connected to the clamping holes 141 in the cooperation method so that the first fixing part 100 is attached to the vertebral plate 10 which completes the incision 30.

The mounting device provided by the embodiment is used in conjunction with the expanding and shaping device for cervical spinal canal above. In other words, during the surgical process, the holding mechanism 400 can cooperate with the first fixing part 100 in the folded state in a clamping way. The holding mechanism 400 can be separately snapped with the clamping holes 141 of opposite two sides of the first fixing part 100. At the same time, the end part of the holding mechanism 400 can also form a contact interference with the second fixing part 200 in the folded state, so as to ensure that the first fixing part 100 and the second fixing part 200 in the folded state can be extended into the incision 30 so that the extension member 102 of the first fixing part 100 can be attached to the incision 30.

In the preferred embodiment of the present disclosure, the holding mechanism 400 includes the holder 401 and the fastening mechanism 402. The holder 401 is provided with the clamping ends 411, wherein the clamping ends 411 can clamp two sides of the first fixing part 100, and the clamping ends 411 can be snapped respectively with each of the two clamping holes 141. The fastening mechanism 402 can cooperate with the fastener 300, and the fastening mechanism 402 is configured to drive the fasteners 300 to pass through the first fixing hole and then to be nailed into the vertebral plate 10.

In this embodiment, the holder 401 serves as a clamping and conveying mechanism, which can clamp and fix the first fixing part 100 in the folded state. At the same time, the fastening mechanism 402 serves as an operational tool for the fasteners 300. The fastening mechanism 402 nails the fasteners 300 into a device which completes the insertion in the incision 30, that is, the end of the fastening mechanism 402 can be snapped with the fasteners 300, and the fastening mechanism 402 can drive the fasteners 300 into the first fixing hole. At this point, the fastening mechanism 402 can drive the fastener 300 to be screwed into the vertebral plate 10. When the vertebral plate 10 is nailed, the fastening mechanism 402 is withdrawn, and the holder 401 is utilized for lifting in the vertical direction. When lifted to a preset distance, the clamping end 411 is separated from the first fixing part 100 and the second fixing part 200 is flipped, so that the step 212 of the second fixing part 200 is positioned and snapped to the lateral mass 20, and the positioning member 202 is attached and positioned to the lateral mass 20 at the same time. After the fastening mechanism is then utilized to nail the fasteners 300 into the lateral mass 20 along the second fixing hole, the operation of one side of the vertebral plate 10 is completed. The other side of the vertebral plate 10 is then operated in the same way.

Optionally, the clamping end 411 can be provided with two clamping bumps arranged opposite each other, wherein the shape of the clamping bumps is adapted to the clamping holes 141, that is, the clamping protrusions 4711 are separately inserted into the two clamping holes 141, and the clamping bumps are snapped and fixed with the clamping holes 141 at this point.

In the preferred embodiment of the present disclosure, the holder 401 includes an adjusting part 421, and a first clamping part 431 and a second clamping part 441 hinged with each other, wherein the first clamping part 431 and the second clamping part 441 can be rotated relative to a hinged point 451 to adjust a clamping range of the clamping ends 411; and one end of the adjusting part 421 is rotationally connected to one end of the first clamping part 431 away from the clamping ends 411, and the other end of the adjusting part 421 can be snapped with one end of the second clamping part 441 away from the clamping ends 411 to adjust the first clamping part 431 and the second clamping part 441 to be in a rotated or fixed state.

In the embodiment, the first clamping part 431 and the second clamping part 441 can adopt a structure similar to pincer, that is, opening and closing operations are performed by the cross-hinged first clamping part 431 and second clamping part 441. At the same time, the ends of the first clamping part 431 and the second clamping part 441 are separately provided with the clamping bumps arranged oppositely, and orientations of the clamping bumps are opposite. After the first clamping part 431 and the second clamping part 441 are separately clamped on two ends of the fixing member 101, the two clamping bumps can be inserted in the clamping holes 141. In order to ensure relative stability between the first clamping part 431 and the second clamping part 441, one end of the first clamping part 431 and the second clamping part 441 away from the clamping ends 411 is provided with the adjusting part 421, wherein the adjusting part 421 has two states of fixing and opening. When the adjusting part 421 is rotated along the first clamping part 431 to be snapped with the second clamping part 441, the adjusting part 421 can block the first clamping part 431 and the second clamping part 441 into a fixed state, that is, at this point, the first clamping part 431 and the second clamping part 441 cannot carry out an open operation, which ensures the stability of conveying the first fixing part 100 and the second fixing part 200. When conveyed in position, the adjusting part 421 is separated from the second clamping part 441. At this point, the doctor can separate the clamping ends 411 from the clamping holes 141 by holding the first clamping part 431 and the second clamping part 441. Then, it only needs to take out the holder 401.

Optionally, the adjusting part 421 can utilize a toothed plate, that is, one end of the adjusting part 421 is hinged to the first clamping part 431, and one side of the adjusting part 421 is uniformly provided with fixed teeth. One end of the second clamping part 441 away from the clamping ends 411 is provided with the groove, and a tooth space is arranged on the bottom of the groove. When the first clamping part 431 and the second clamping part 441 complete the clamping operation relative to the hinged point 451, the adjusting part 421 is utilized to be rotated relative to the first clamping part 431, so that the adjusting part 421 is extended into the groove of the second clamping part 441. At the same time, the adjusting part 421 is snapped and fixed with the tooth space by utilizing fixed teeth, and thus the first clamping part 431 and the second clamping part 441 are fixed.

In the preferred embodiment of the present disclosure, the holder 401 further includes a first elastic plate 461 and a second elastic plate 471. An adjusting space from the hinged point 451 to the adjusting part 421 is formed by the first clamping part 431 and the second clamping part 441, and the first elastic plate 461 and the second elastic plate 471 are located within the adjusting space. The first elastic plate 461 is in an arcuate structure. One end of the first elastic plate 461 is provided with a slot 4611. One end of the first elastic plate 461 away from the slot 4611 is connected to the first clamping part 431. The second elastic plate 471 is in an arcuate structure. One end of the second elastic plate 471 is provided with a protrusion 4711. One end of the second elastic plate 471 away from the protrusion 4711 is connected to the second clamping part 441. The second elastic plate 471 can be inserted into the first elastic plate 461 in the cooperation method by the slot 4611 and the protrusion 4711. The first elastic plate 461 and the second elastic plate 471 provide an elastic tendency to move the first clamping part 431 and the second clamping part 441 away from each other, so that the clamping ends 411 have a tendency to move relatively close together.

In this embodiment, the clamping space and the adjusting space are formed between the first clamping part 431 and the second clamping part 441 which are bounded by the hinged point 451. The adjusting space serves as a butt space formed by inner walls of the first clamping part 431 and the second clamping part 441. The first elastic plate 461 is arranged on the inner wall of the first clamping part 431. One end of the first elastic plate 461 is connected to the inner wall of the first clamping part 431, and the other end of the first elastic plate 461 is in a free state. The first elastic plate 461 is in the arcuate structure, and the first elastic plate 461 is of an inwardly concave arcuate structure. Similarly, the second elastic plate 471 is arranged on the inner wall of the second clamping part 441. One end of the second elastic plate 471 is connected to the inner wall of the second clamping part 441, and the other end of the second elastic plate 471 is in a free state. The second elastic plate 471 is in the arcuate structure, and the second elastic plate 471 is of an inwardly concave arcuate structure. The first elastic plate 461 can be butted and snapped with the second elastic plate 471 by the protrusion 4711 and the groove. That is, when the first elastic plate 461 is connected to the second elastic plate 471, the first elastic plate 461 and the second elastic plate 471 have an elastic force that drives the first clamping part 431 to be away from the second clamping part 441 at this point. The first clamping part 431 and the second clamping part 441 serve as the pincer structure. The first elastic plate 461 and the second elastic plate 471 are located in the adjusting space of the hinged point 451 away from the clamping ends 411, that is, at this point, the clamping ends 411 of the first clamping part 431 and the second clamping part 441 have the force to close to each other so that the first clamping part 431 and the second clamping part 441 can clamp and fix the clamping holes 141 of the first fixing part 100. When the clamping end 411 needs to be separated from the clamping hole 141, the doctor needs to overcome the force of the first elastic plate 461 and the second elastic plate 471 to be able to drive the clamping ends 411 in a spreading motion, so as to complete the separation between the clamping end 411 and the clamping hole 141, which ensures the stability of the clamping.

Finally, it should be noted that the above embodiments are only used to illustrate the technical solutions of the present disclosure and are not intended to be a limitation thereof. Notwithstanding the detailed description of the present disclosure with reference to the foregoing embodiments, it should be understood by those of ordinary skill in the art that it is still possible to modify the technical solutions recorded in the foregoing embodiments or to replace some or all the technical features therein with equivalent ones. These modifications or replacements do not take the essence of the corresponding technical solutions out of the scope of the technical solutions of the embodiments of the present disclosure.

The invention claimed is:

1. An expanding and shaping device for a cervical spinal canal, configured to expand, shape, and fix a vertebral plate and a lateral mass formed by incising the cervical spinal canal, and a vertical incision is formed between the vertebral plate and the lateral mass, wherein the expanding and shaping device for cervical spinal canal comprises:

a first fixing part;

a second fixing part; and fasteners, wherein the first fixing part is hinged to the second fixing part, wherein the first fixing part can be attached to a side wall of the vertebral plate, and the second fixing part is configured to be attached to a side surface of the lateral mass towards the vertebral plate, wherein a first fixing hole is arranged on the first fixing part, and the fasteners are configured to pass through the first fixing hole to connect the vertebral plate, and a passing-through direction of the fasteners is consistent with a direction of the incision; and a second fixing hole is arranged on the second fixing part, wherein the fasteners are configured to pass through the second fixing hole to connect the lateral mass, wherein the first fixing part comprises a fixing member and an extension member, wherein the fixing member is fixedly connected to the extension member, the fixing member is provided with an inclined concave surface;

the fixing member is configured to be attached to a side wall of the vertebral plate by the inclined concave surface; and one side of the fixing member away from the inclined concave surface is arranged in a horizontal plane, wherein the first fixing hole passes vertically through the horizontal plane, and the fasteners can pass through the inclined concave surface from the horizontal plane so that the fasteners are configured to be tightly connected to the vertebral plate, and the extension member is arranged parallel to the incision so that the extension member can extend along a surface of the incision, wherein the second fixing part comprises a hinge member and a positioning member, wherein the hinge member is connected to the positioning member, and the hinge member is provided with a rotating shaft, wherein the extension member is rotationally connected to the hinge member by the rotating shaft so that the first fixing part and the second fixing part are in a folded state or an unfolded state, the positioning member is configured to be attached to a surface of the lateral mass, the second fixing hole passes through the positioning member; and the fasteners are configured to be connected to the lateral mass by the second fixing hole to fix the positioning member on the lateral mass, wherein the positioning member is provided with a step, and the positioning member is configured to abut against one side of the lateral mass provided with the incision by the step so as to be positioned for fixation, and wherein one side of the positioning member away from the step is provided with a first inclined surface, and one end of the extension member away from the fixing member is provided with a second inclined surface, wherein in the unfolded state, the extension member abuts and is limited by the first inclined surface of the positioning member by the second inclined surface, so as to limit the extension member to be in planar contact with the incision of the vertebral plate by the positioning member.

2. The expanding and shaping device for the cervical spinal canal of claim 1, wherein one side of the first fixing part towards the second fixing part is provided with an accommodation groove, wherein the second fixing part can be attached and fixed with the accommodation groove, and wherein the expanding and shaping device further comprises clamping holes configured for cooperating with an external holder are arranged on two opposite sides of the first fixing part.

* * * * *